(12) United States Patent
Kumar et al.

(10) Patent No.: US 8,788,028 B2
(45) Date of Patent: **\*Jul. 22, 2014**

(54) PARASYMPATHETIC STIMULATION TO ENHANCE TACHYARRHYTHMIA DETECTION

(75) Inventors: Arun Kumar, Blaine, MN (US);
Shailesh Kumar Vishnu Musley, Blaine, MN (US)

(73) Assignee: Medtronic, Inc., Minneapolis, MN (US)

( \* ) Notice: Subject to any disclaimer, the term of this patent is extended or adjusted under 35 U.S.C. 154(b) by 451 days.

This patent is subject to a terminal disclaimer.

(21) Appl. No.: 12/845,505

(22) Filed: Jul. 28, 2010

(65) Prior Publication Data
US 2012/0029586 A1  Feb. 2, 2012

(51) Int. Cl.
*A61B 5/04* (2006.01)

(52) U.S. Cl.
USPC .......................................................... 600/518

(58) Field of Classification Search
None
See application file for complete search history.

(56) References Cited

U.S. PATENT DOCUMENTS

| | | |
|---|---|---|
| 4,951,667 A | 8/1990 | Markowitz et al. |
| 5,154,170 A | 10/1992 | Bennett et al. |
| 5,203,326 A | 4/1993 | Collins |
| 5,243,980 A | 9/1993 | Mehra |
| 5,320,642 A | 6/1994 | Scherlag |
| 5,330,507 A | 7/1994 | Schwartz |
| 5,356,425 A | 10/1994 | Bardy et al. |
| 5,403,356 A | 4/1995 | Hill et al. |
| 5,411,531 A | 5/1995 | Hill et al. |
| 5,507,784 A | 4/1996 | Hill et al. |
| 5,620,468 A | 4/1997 | Mongeon et al. |
| 5,683,429 A | 11/1997 | Mehra |
| 5,855,592 A | 1/1999 | McGee et al. |
| 5,876,422 A | 3/1999 | van Groeningen |
| 5,978,700 A | 11/1999 | Nigam |

(Continued)

FOREIGN PATENT DOCUMENTS

| | | |
|---|---|---|
| EP | 0547734 A2 | 6/1993 |
| EP | 0756507 B1 | 2/1999 |

(Continued)

OTHER PUBLICATIONS

Wilkoff et al., Critical Analysis of Dual-Chamber Implantable Cardioverter-Defibrillator Arthythmial Detection: Results and Technical Considerations, Circulation, (Jan. 23, 2001), pp. 381-386, vol. 103, No. 3.

(Continued)

*Primary Examiner* — Brian T Gedeon
*Assistant Examiner* — Ankit Tejani
(74) *Attorney, Agent, or Firm* — Michael C. Soldner

(57) ABSTRACT

This disclosure is directed toward techniques for classifying a tachycardia as supraventricular tachycardia or ventricular tachycardia. A method comprises detecting a tachycardia based on at least one value of a cardiac interval, delivering vagal stimulation in response to the detection of the tachycardia, sensing a physiological parameter other than the cardiac interval during or subsequent to delivering the vagal stimulation, and classifying the tachycardia as supraventricular or ventricular based on the sensed physiological parameter. In some examples, the method includes sensing a response of a physiological parameter other than cardiac rate to the vagal stimulation, such as pressure or a morphological characteristic of the cardiac electrical waveform. The method may include providing an indication to a user based on the classification of supraventricular tachycardia, or delivery of appropriate electrical therapy based on the classification of ventricular tachycardia or ventricular fibrillation.

32 Claims, 9 Drawing Sheets

(56) References Cited

U.S. PATENT DOCUMENTS

| | | | |
|---|---|---|---|
| 6,256,537 | B1 | 7/2001 | Stoop et al. |
| 6,393,316 | B1 | 5/2002 | Gillberg et al. |
| 6,438,421 | B1 | 8/2002 | Stahmann et al. |
| 6,611,713 | B2 | 8/2003 | Schauerte |
| 6,731,978 | B2 | 5/2004 | Olson et al. |
| 7,138,607 | B2 | 11/2006 | Wang et al. |
| 7,139,607 | B1 | 11/2006 | Shelchuk |
| 7,225,019 | B2 | 5/2007 | Jahns et al. |
| 7,245,967 | B1 | 7/2007 | Shelchuk |
| 7,403,819 | B1 | 7/2008 | Shelchuk et al. |
| 2002/0035335 | A1 | 3/2002 | Schauerte |
| 2003/0229380 | A1* | 12/2003 | Adams et al. ............ 607/9 |
| 2005/0119704 | A1 | 6/2005 | Peters et al. |
| 2006/0206159 | A1 | 9/2006 | Moffitt et al. |
| 2006/0224202 | A1 | 10/2006 | Moffitt et al. |
| 2007/0083242 | A1 | 4/2007 | Mazgalev et al. |
| 2007/0150014 | A1* | 6/2007 | Kramer et al. ............ 607/17 |
| 2007/0197928 | A1* | 8/2007 | Kim et al. ............ 600/515 |
| 2008/0091240 | A1 | 4/2008 | Ben-David et al. |
| 2008/0269819 | A1 | 10/2008 | Zhou |
| 2009/0062667 | A1* | 3/2009 | Fayram et al. ............ 600/486 |
| 2010/0036447 | A1 | 2/2010 | Zhang et al. |

FOREIGN PATENT DOCUMENTS

| | | |
|---|---|---|
| EP | 1426078 A1 | 6/2004 |
| EP | 1870129 A1 | 12/2007 |
| WO | 2007142563 A1 | 12/2007 |
| WO | 2008144125 A1 | 11/2008 |

OTHER PUBLICATIONS

International Search Report, PCT/US/2008/059723, Aug. 27, 2008, 6 pages.
Written Opinion, PCT/US/2008/059723, Aug. 27, 2008, 7 pages.
International Preliminary Report on Patentability, PCT/US/2008/059723, Oct. 27, 2009, 8 pages.
Office Action for U.S. Appl. No. 11/740,565, mailed Dec. 30, 2009, 8 pages.
Responsive Amendment to Office Action for U.S. Appl. No. 11/740,565, filed Apr. 29, 2010, 10 pages.
Final Office Action for U.S. Appl. No. 11/740,565, mailed Jan. 21, 2011, 9 pages.
Responsive Amendment to Office Action for U.S. Appl. No. 11/740,565, filed Mar. 21, 2011, 8 pages.
Aydin M. Bilgutay et al., "Vagal tuning a new concept in the treatment of supraventricular arrhythmias, angina pectoris, and heart failure," Journal of Thoracic and Cardiovascular Surgery, vol. 56, No. 1 (Jul. 1968) pp. 71-82.
International Search Report and Written Opinion of international application No. PCT/US2011/033566, dated Jun. 14, 2011, 9 pp.
Henning et al., "Vagal nerve stimulation increases right ventricular contraction and relaxation and heart rate," Cardiovascular Research 32: 846-853, 1996.
Rossi et al., "Post-operative atrial fibrillation management by selective epicardial vagal fat pad stimulation," J Interv Card Electrophysiol (2009) 24:37-45.
Bianchi et al., "Endocardial Transcatheter Stimulation of the AV Nodal Fat Pad: Stabilization of Rapid Ventricular Rate Response During Atrial Fibrillation in Left Ventricular Failure," Journal of Cardiovascular Electrophysiology 20 (1):103-105, Jan. 2009.
Schwartz et al., "Long term vagal stimulation in patients with advanced heart failure: first experience in man," Eur J. Heart Fail, Sep. 2008;10(9): 884-91.
Poole et al., "Prognostic importance of defibrillator shocks in patients with heart failure," N Engl J. Med. 2008; 359 (10):1009-17.
Nunain et al., "Limitations and late complications of third-generation automatic cardioverter-defirillators," Circulation 1995;91(8):2204-2213.
Nanthakumar et al., "Inappropriate therapy from atrial fibrillation and sinus tachycardia in automated implantable cardioverter defibrullators," Am Heart J., 2000; 139(5):797-803.
Kale et al., "Atrial septal pacing in the prevention of paroxysmal atrial fibrillation refractory to antiarrhythmic drugs," International Journal of Cardiology 82(2):167-175, Feb. 2002.
Gupta, "Suppression of Paroxysmal Atrial Fibrillation by Pacing," Indian Pacing and Electrophysiology Journal (ISSN 0972-6292), 3(2):45-46, 2003.
The National Heart, Lung, and Blood Institute for working group on Atrial fibrillation: Current understanding research imperatives, J Am Coll Cardiol 1993; 22(7):1830-34.
Ogawa et al., "Acute Effects of Different Atrial Pacing Sites in Patients with Atrial Fibrillation: Comparison of Single Site and Biatrial Pacing," PACE 2001; 24:1470-78.
Murgatroyd, "Pills and Pulses": Hybrid Therapy for Atrial Fibrillation, J Cardiovasc Electrophysiol vol. 13, pp. S40-S46, Jan. 2002, Suppl.
Carlsson et al., "Therapy of Atrial Fibrillation: Rhythm Control Versus Rate Control," PACE 2000; 23: 891-903.
Harvey et al., "Radiofrequency catheter ablation for atrial fibrillation," Coronary Artery Disease 1995; 6(2):115-20.
Rosenqvist et al., "Relative Importance of Activation Sequence Compared to Atrioventricular Synchrony in Left Ventricular Function," Am J Cardiol 1991; 67:148-156.
Vardas et al., "AAIR versus DDDR Pacing in Patients with Impaired Sinus Node Chronotropy: An Echocardiographic and Cardiopulmonary Study," PACE 1997; 20:1762-64.
Israel et al, "Atrial Pacing in the Prevention of Paroxysmal Atrial Fibrillation: First Results of a New Combined Algorithm," PACE 2000; 23[Pt.II]: 1888-1890.
Saksena et al., "Prevention of Atrial fibrillation by pacing," In Barold SS and Mugica J (Eds), 1998. Recent Advances in Cardiac Pacing: Goals for the 21st century. Armonk, NY. Futura Publishing Company Inc., pp. 101-114.
Levine et al.,"Pacing for the Suppression of Paroxysmal Atrial Fibrillation in an 87-year-old Patient," Indian Pacing Electrophysiol. J. 2003; 3: 88.
Purerfellner et al., "Accuracy of Atrial Tachyarrhythmia Detection in Implantable Devices with Arrhythmia Therapies," PACE 2004; 27(7):983-992.
Tosato et al., "Closed-loop control of the heart rate by electrical stimulation of the vagus nerve," Med Biol Eng Comp 44(3):161-169, 2006.
Zhang et al., "Optimal ventricular rate slowing during atrial fibrillation by feedback AV nodal-selective vagal stimulation," Am J Physiol Heart Circ Physiol 2002; 282(3):H1102-H1110.
Zhang et al., "Chronic Atrioventricular Nodal Vagal Stimulation: First Evidence for Long-Term Ventricular Rate Control in Canine Atrial Fibrillation Model," Circulation 2005; 112:2904-2911.
Zhuang et al., "Ventricular Rate Control by Selective Vagal Stimulation is Superior to Rhythm Regularization by Atrioventricular Nodal Ablation and Pacing During Atrial Fibrillation," Circulation 2002; 106(14):1853-1858.
U.S. Appl. No. 12/496,528, by Stefano Bianchi, filed Jul. 1, 2009.
International Preliminary Report on Patentability from corresponding PCT Application Serial No. PCT/US2011/033566 dated Feb. 7, 2013 (6 pages).

* cited by examiner

PARASYMPATHETIC STIMULATION TO ENHANCE TACHYARRHYTHMIA DETECTION

TECHNICAL FIELD

The invention relates to medical devices and, more particularly, to medical devices that deliver electrical stimulation therapy.

BACKGROUND

When functioning properly, a heart maintains its own intrinsic rhythm, and is capable of pumping adequate blood throughout a circulatory system. This intrinsic rhythm is a function of intrinsic signals generated by the sinoatrial node, or SA node, located in the upper right atrium. The SA node periodically depolarizes, which in turn causes the atrial heart tissue to depolarize such that right and left atria contract as the depolarization travels through the atrial heart tissue. The atrial depolarization signal is also received by the atrioventricular node, or AV node, which, in turn, e.g., after a brief delay of approximately 0.12 seconds, triggers a subsequent ventricular depolarization signal that travels through and depolarizes the ventricular heart tissue causing the right and left ventricles to contract.

Some patients, however, have irregular cardiac rhythms, referred to as cardiac arrhythmias. Cardiac arrhythmias result in diminished blood circulation because of diminished cardiac output. Atrial fibrillation is a common cardiac arrhythmia that reduces the pumping efficiency of the heart. Atrial fibrillation is characterized by rapid, irregular, uncoordinated depolarizations of the atria. These depolarizations may not originate from the SA node, but may instead originate from an arrhythmogenic substrate, such as an ectopic focus, within the atrial heart tissue. The reduced pumping efficiency due to atrial fibrillation requires the ventricle to work harder, which is particularly undesirable in sick patients that cannot tolerate additional stress. As a result of atrial fibrillation, patients must typically limit activity and exercise.

Other types of cardiac arrhythmias originate in the ventricles. Ventricular arrhythmias may compromise pumping efficiency even more drastically than atrial arrhythmias. Some ventricular arrhythmias are treated using defibrillation and/or cardioversion therapy.

In some cases, an atrial fibrillation or other atrial tachyarrhythmia induces rapid and irregular ventricular heart rhythms. Rapid and/or irregular atrial depolarization signals associated with atrial tachyarrhythmia are received by the AV node, and may be conducted to the ventricles. Such induced ventricular arrhythmias compromise pumping efficiency even more drastically than atrial arrhythmias, and are referred to as supraventricular tachycardia (SVT). Although SVT is not usually treatable by delivery of defibrillation and/or cardioversion therapy to the ventricles, in some cases a medical device misclassifies an SVT as a ventricular tachyarrhythmia, and inappropriately delivers such therapies to the ventricles in response to an SVT.

SUMMARY

In general, the disclosure describes techniques for classifying a detected tachyarrhythmia as ventricular or supraventricular. More particularly, the disclosure describes techniques for classifying the tachyarrhythmia based on a response of a physiological parameter to vagal stimulation. In some examples, the techniques involve sensing a response of a physiological parameter other than cardiac rate to the vagal stimulation, such as pressure or a morphological characteristic of the cardiac electrical waveform.

In one example, the invention is directed to a method comprising detecting a tachycardia based on at least one value of a cardiac interval, delivering vagal stimulation in response to the detection of the tachycardia, sensing a physiological parameter other than the cardiac interval during or subsequent to delivering the vagal stimulation, and classifying the tachycardia as supraventricular or ventricular based on the sensed physiological parameter.

In another example, the invention is directed to a system comprising a stimulation generator configured to deliver vagal stimulation to a patient, a processor configured to detect a tachycardia based on at least one value of a cardiac interval, and an arrhythmia discrimination module configured to control the stimulation generator to deliver the vagal stimulation in response to the detection of the tachycardia, detect a physiological parameter other than the cardiac interval during or subsequent to the stimulation generator delivering the vagal stimulation, and classify the tachycardia as supraventricular or ventricular based on the sensed physiological parameter.

In another example, the invention is directed to a computer-readable medium containing instructions. The instructions cause a programmable processor to detect a tachycardia based on at least one value of a cardiac interval, deliver vagal stimulation in response to the detection of the tachycardia, sense a physiological parameter other than the cardiac interval during or subsequent to delivering vagal stimulation, and classify the tachycardia as supraventricular or ventricular based on the sensed physiological parameter.

In another example, the invention is directed to a system comprising means for detecting a tachycardia based on at least one value of a cardiac interval, means for delivering vagal stimulation in response to the detection of the tachycardia, means for sensing a physiological parameter other than the cardiac interval during or subsequent to delivering vagal stimulation, and means for classifying the tachycardia as supraventricular or ventricular based on the sensed physiological parameter.

In another example, the invention is directed to a method comprising detecting a tachycardia based on at least one value of a cardiac interval, delivering vagal stimulation in response to the detection of the tachycardia, sensing a physiological parameter during or subsequent to delivering vagal stimulation, classifying the tachycardia as supraventricular based on the sensed physiological parameter, and providing an indication to the user based on the classification of supraventricular tachycardia.

The details of one or more examples of the invention are set forth in the accompanying drawings and the description below. Other features, objects, and advantages of the invention will be apparent from the description and drawings, and from the claims.

DETAILED DESCRIPTION

The vagus nerve innervates various parts of the cardiovascular system, including the sinoatrial (SA) node and the atrioventricular (AV) node. Stimulation of the vagus nerve may result in decreased activity of the SA and AV nodes. Accordingly, vagal stimulation may be used to determine whether a cardiac rhythm, e.g., an arrhythmia, originates above the ventricular tissue (i.e., is supraventricular in origin) or within the ventricular tissue (i.e., is ventricular in origin).

For example, transient blocking of AV nodal conduction may be attained by stimulating the parasympathetic, e.g., vagal, fibers going to the AV node. The difference between the ventricular rate before and after AV block may be used to determine whether the rhythm is supraventricular or ventricular in origin. If there is no significant change in the rhythm, e.g., the fluctuation is below a threshold, during or subsequent to the AV nodal vagal stimulation, the rhythm is likely ventricular in origin. Whereas, with a rhythm of supraventricular origin, transient AV block may prevent electrical activity from being transmitted to the ventricles and reduce the ventricular rate.

Differentiation between supraventricular tachycardias (SVTs) and ventricular tachycardias (VTs) may reduce inappropriate detections of SVT as VT. This may be particularly important, since delivery of therapy to the ventricles, such as a cardioversion or defibrillation pulse, in response to a SVT will likely be ineffective and is undesired.

Due to the close relation of vagal innervation to the AV node, stimulation of the AV node and/or neural fibers proximate to the AV node may provide vagal stimulation. Additionally, AV nodal vagal stimulation may block atrial signals from propagating to the ventricles, which may be particularly helpful in distinguishing SVT from VT. Hereinafter, vagal stimulation will be primarily described with respect to the example of AV nodal stimulation. However, in other examples, vagal stimulation may be delivered at other locations. For example, vagal stimulation may be applied at one or both of the SA and AV node fat pads, applied intracardially or epicardially, and/or applied directly to the vagus nerve or the cardiac branch of the vagus nerve via, for example, a cuff electrode that at least partially surrounds the nerve. In some examples, vagal stimulation may be applied during the atrial refractory period to prevent induction of SVT.

The various techniques for discriminating SVT from VT described herein may be performed in an implantable medical device (IMD), such as an implantable pacemaker, defibrillator, cardioverter, or any combination thereof. An IMD will be described herein for purposes of example. Although, in other examples, these discrimination techniques may be performed by an external device, e.g., an external programmer that communicates with an IMD.

Figure 1:
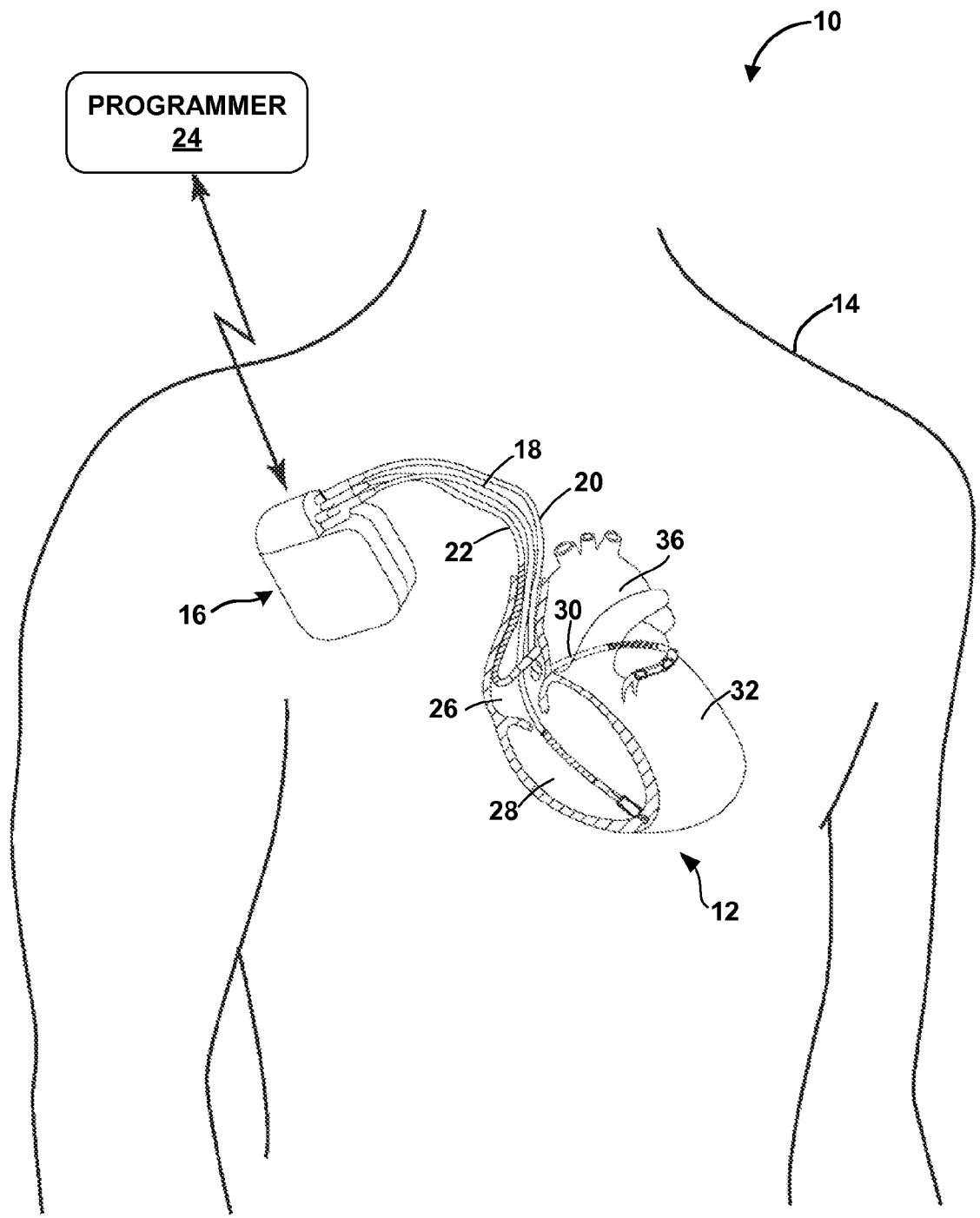
FIG. 1 is a conceptual diagram illustrating an example therapy system comprising an implantable medical device (IMD) that may be used to monitor one or more physiological parameters of a patient and/or provide therapy to the heart of a patient.

FIG. 1 is a conceptual diagram illustrating an example therapy system 10 that may be used to monitor one or more physiological parameters of patient 14 and/or to provide therapy to heart 12 of patient 14. Therapy system 10 includes an implantable medical device (IMD) 16, which is coupled to leads 18, 20, and 22, and programmer 24. IMD 16 may be an implantable pacemaker that provides electrical signals to heart 12 via electrodes coupled to one or more of leads 18, 20, and 22. In addition to pacing therapy, IMD 16 may deliver AV nodal stimulation and/or neurostimulation signals. In some examples, IMD 16 may also include cardioversion and/or defibrillation functionalities. Patient 14 is ordinarily, but not necessarily, a human patient.

Leads 18, 20, 22 extend into the heart 12 of patient 14 to sense electrical activity of heart 12 and/or deliver electrical stimulation to heart 12. In the example shown in FIG. 1, right ventricular (RV) lead 18 extends through one or more veins (not shown), the superior vena cava (not shown), and right atrium 26, and into right ventricle 28. RV lead 18 may be used to deliver RV pacing to heart 12. Left ventricular (LV) lead 20 extends through one or more veins, the vena cava, right atrium 26, and into the coronary sinus 30 to a region adjacent to the free wall of left ventricle 32 of heart 12. LV lead 20 may be used to deliver LV pacing to heart 12.

Right atrial (RA) lead 22 extends through one or more veins and the vena cava, and into the right atrium 26 of heart 12. RA lead 22 may be positioned in the inferior portion of right atrium 26. In some examples, RA lead 22 may be positioned in the posterior portion of right atrium 26 around the coronary sinus ostium, such as posteriorly to the coronary sinus ostium, and along the septum that separates right atrium 26 and left atrium 36. For example, RA lead 22 may be positioned such that RA lead 22 may sense electrical activity within right atrium 26, pace right atrium 26, and also deliver a stimulation signal to or proximate to the AV node, e.g., to or proximate to the AV nodal vagal fat pad.

In some examples, system 10 may additionally or alternatively include one or more leads or lead segments (not shown in FIG. 1) that deploy one or more electrodes within the vena cava or other vein, or within or near the aorta. Furthermore, in some examples, system 10 may additionally or alternatively include one or more additional intravenous or extravascular leads or lead segments that deploy one or more electrodes epicardially, e.g., near an epicardial fat pad, or proximate to the vagus nerve. In other alternative examples, system 10 need not include one of ventricular leads 18 and 20.

Additionally, IMD 16 is not limited to delivering stimulation to or proximate to the AV node, e.g., to or proximate to the AV nodal vagal fat pad, via RA lead 22. Instead, system 10 may include any leads and electrodes suitable for delivering AV nodal fat pad stimulation. For example, IMD 16 may deliver AV nodal vagal stimulation by means of a lead carrying electrodes located in the coronary sinus, adjacent the posterior groove and/or by means of epicardial or myocardial electrodes applied on or adjacent to the AV nodal fat pad, as described in U.S. Pat. No. 5,356,425 to Bardy et al., which issued on Oct. 18, 1994 and is entitled, "METHOD AND APPARATUS FOR TREATMENT OF ATRIAL FIBRILLATION AND FLUTTER," and is incorporated herein by reference in its entirety. As another example, IMD 16 may deliver AV nodal vagal stimulation by means of leads carrying electrodes located in the right pulmonary artery, right atrium and/or coronary sinus and/or by means of vagal nerve stimulation using nerve bundle electrodes, as described in U.S. Pat. No. 5,243,980 to Mehra, which issued on Sep. 14, 1993 and is entitled, "METHOD AND APPARATUS FOR DISCRIMINATION OF VENTRICULAR AND SUPRAVENTRICULAR TACHYCARDIA," and is incorporated herein by reference in its entirety. As another example, IMD 16 may deliver AV nodal vagal stimulation by means of an atrial lead including an electrode fixed, e.g., via a screw-in helical wire, on or proximate to the AV node, e.g., sufficiently close to the His and/or in the triangle of Koch, as described in U.S. Pat. No. 6,256,537 to Stoop et al., which issued on Jul. 3, 2001 and is entitled, "PACEMAKER SYSTEM WITH INHIBITION OF AV NODE FOR RATE REGULATION DURING ATRIAL FIBRILLATION," and is incorporated herein by reference in its entirety. In some examples, system 10 may include one or more leads dedicated to delivering vagal stimulation.

IMD 16 may sense electrical signals attendant to the depolarization and repolarization of heart 12 via electrodes (not shown in FIG. 1) coupled to at least one of the leads 18, 20, 22. In some examples, IMD 16 provides pacing pulses to heart 12 based on the electrical signals sensed within heart 12. The configurations of electrodes used by IMD 16 for sensing and pacing may be unipolar or bipolar.

IMD 16 may also provide neurostimulation therapy, defibrillation therapy and/or cardioversion therapy via electrodes located on at least one of the leads 18, 20, 22. IMD 16 may detect arrhythmia of heart 12, such as a high ventricular rate, and deliver vagal stimulation, e.g., AV nodal vagal stimulation, to help classify the high cardiac rate as SVT or VT. IMD 16 may deliver defibrillation therapy, cardioversion therapy, and/or anti-tachycardia pacing (ATP) based on the classification. For example, IMD 16 may deliver defibrillation therapy to heart 12 in the form of electrical pulses upon classifying the high cardiac rate as ventricular fibrillation of ventricles 28 and 32. In some examples, IMD 16 may be programmed to deliver a progression of therapies, e.g., pulses with increasing energy levels, until a fibrillation of heart 12 is stopped. As another example, IMD 16 may similarly deliver cardioversion or ATP in response to classifying the high cardiac rate as VT, such as tachycardia of ventricles 28 and 32. As yet another example, IMD 16 may not deliver a therapy in response to classifying the high cardiac rate as SVT originating above ventricles 28 and 32.

In some examples, programmer 24 comprises a handheld computing device, computer workstation, or networked computing device. Programmer 24 includes a user interface that presents information to and receives input from a user. It should be noted that the user may also interact with programmer 24 remotely via a networked computing device.

A user, such as a physician, technician, surgeon, electrophysiologist, other clinician, or patient, interacts with programmer 24 to communicate with IMD 16. For example, the user may interact with programmer 24 to retrieve physiological or diagnostic information from IMD 16. A user may also interact with programmer 24 to program IMD 16, e.g., select values for operational parameters of the IMD.

For example, the user may use programmer 24 to retrieve information from IMD 16 regarding the rhythm of heart 12, trends therein over time, or arrhythmic episodes. In some examples, the user of programmer 24 may receive an indication that a high ventricular rate was classified as a SVT and/or that delivery of therapy to the ventricles has been withheld. As another example, the user may use programmer 24 to retrieve information from IMD 16 regarding other sensed physiological parameters of patient 14 or information derived from sensed physiological parameters, such intracardiac or intravascular pressure, activity, posture, respiration, tissue perfusion, heart sounds, cardiac electrogram (EGM), intracardiac impedance, or thoracic impedance. As another example, the user may use programmer 24 to retrieve information from IMD 16 regarding the performance or integrity of IMD 16 or other components of system 10, such as leads 18, 20 and 22, or a power source of IMD 16. As another example, the user may interact with programmer 24 to program, e.g., select parameters for, therapies provided by IMD 16, such AV nodal stimulation and, optionally, pacing, cardioversion and/or defibrillation.

IMD 16 and programmer 24 may communicate via wireless communication using any techniques known in the art. Examples of communication techniques may include, for example, low frequency or radiofrequency (RF) telemetry, but other techniques are also contemplated. In some examples, programmer 24 may include a programming head that may be placed proximate to the patient's body near the IMD 16 implant site in order to improve the quality or security of communication between IMD 16 and programmer 24.

Figure 2:
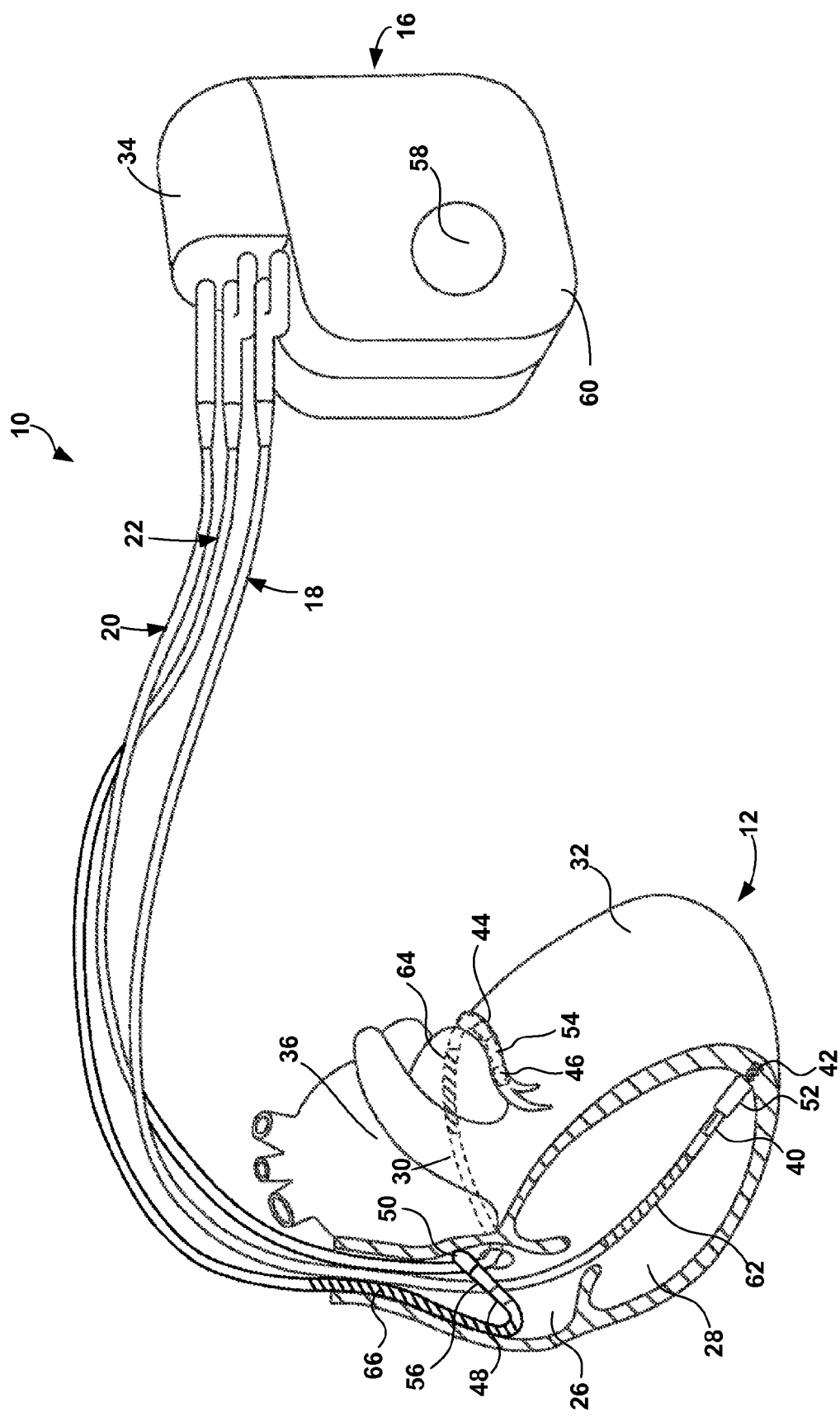
FIG. 2 is a conceptual diagram further illustrating the IMD and leads of the system of FIG. 1 in conjunction with the heart.

FIG. 2 is a conceptual diagram illustrating IMD 16 and leads 18, 20, 22 of therapy system 10 in greater detail. Leads 18, 20, 22 may be electrically coupled to a signal generator and a sensing module of IMD 16 via connector block 34. In some examples, proximal ends of leads 18, 20, 22 may include electrical contacts that electrically couple to respective electrical contacts within connector block 34 of IMD 16. In some examples, a single connector, e.g., an IS-4 or DF-4 connector, may connect multiple electrical contacts to connector block 34. In addition, in some examples, leads 18, 20, 22 may be mechanically coupled to connector block 34 with the aid of set screws, connection pins, snap connectors, or another suitable mechanical coupling mechanism.

Each of the leads 18, 20, 22 includes an elongated insulative lead body, which may carry a number of concentric coiled conductors separated from one another by tubular insulative sheaths. Bipolar electrodes 40 and 42 are located adjacent to a distal end of lead 18 in right ventricle 28. In addition, bipolar electrodes 44 and 46 are located adjacent to a distal end of lead 20 in left ventricle 32 and bipolar electrodes 48 and 50 are located adjacent to a distal end of lead 22 in right atrium 26. In the illustrated example, there are no electrodes located in left atrium 36. However, other examples may include electrodes in left atrium 36.

Electrodes 40, 44, and 48 may take the form of ring electrodes, and electrodes 42, 46, and 50 may take the form of extendable helix tip electrodes mounted retractably within insulative electrode heads 52, 54, and 56, respectively. In some examples, one or more of electrodes 42, 46, and 50 may take the form of pre-exposed helix tip electrodes. In other examples, one or more of electrodes 42, 46, and 50 may take the form of small circular electrodes at the tip of a tined lead or other fixation element. Leads 18, 20, 22 also include elongated electrodes 62, 64, 66, respectively, which may take the form of a coil. Each of the electrodes 40, 42, 44, 46, 48, 50, 62, 64, and 66 may be electrically coupled to a respective one of the coiled conductors within the lead body of its associated lead 18, 20, 22, and thereby coupled to respective ones of the electrical contacts on the proximal end of leads 18, 20, 22.

Helix tip electrode 50, which may be extendable or pre-exposed, of RA lead 22 may be inserted into the tissue of right atrium 26 to substantially fix RA lead 22 within right atrium 26. For example, helix tip electrode 50 may be inserted into or proximate to the endocardium of the septum that separates right atrium 26 and left atrium 36 at a posterior portion of right atrium 26. As described previously, RA lead 22 may be positioned such that RA lead 22 may sense electrical activity within right atrium 26, pace right atrium 26, and also deliver a stimulation signal to (or proximate to) the AV node, e.g., to (or proximate to) the AV nodal vagal fat pad. Helix tip electrode 50 may aid in maintaining RA lead 50 in the appropriate position to provide such functionality.

In some examples, as illustrated in FIG. 2, IMD 16 includes one or more housing electrodes, such as housing electrode 58, which may be formed integrally with an outer surface of hermetically-sealed housing 60 of IMD 16 or otherwise coupled to housing 60. In some examples, housing electrode 58 is defined by an uninsulated portion of an outward facing portion of housing 60 of IMD 16. Other division between insulated and uninsulated portions of housing 60 may be employed to define two or more housing electrodes. In some examples, housing electrode 58 comprises substantially all of housing 60. As described in further detail with reference to FIG. 4, housing 60 may enclose a signal generator that generates therapeutic stimulation, such as cardiac pacing pulses and defibrillation shocks, as well as a sensing module for monitoring the rhythm of heart 12.

IMD 16 may sense electrical signals attendant to the depolarization and repolarization of heart 12 via electrodes 40, 42, 44, 46, 48, 50, 58, 62, 64, and 66. The electrical signals are conducted to IMD 16 from the electrodes via the respective leads 18, 20, 22 or, in the case of housing electrode 58, a conductor coupled to housing electrode 58. IMD 16 may sense such electrical signals via any bipolar combination of electrodes 40, 42, 44, 46, 48, 50, 58, 62, 64, and 66. Furthermore, any of the electrodes 40, 42, 44, 46, 48, 50, 58, 62, 64, and 66 may be used for unipolar sensing in combination with housing electrode 58.

In some examples, IMD 16 delivers pacing pulses via bipolar combinations of electrodes 40, 42, 44, 46, 48 and 50 to produce depolarization of cardiac tissue of heart 12. In some examples, IMD 16 delivers pacing pulses via any of electrodes 40, 42, 44, 46, 48 and 50 in combination with housing electrode 58 in a unipolar configuration.

IMD 16 may deliver AV nodal vagal stimulation via electrodes 48, 50, and/or 66 of RA lead 22, e.g., in a bipolar configuration or in a unipolar configuration in combination with housing electrode 58. For example, IMD 16 may detect a high cardiac rate and deliver AV nodal vagal stimulation to help classify the high cardiac rate as SVT or VT.

Furthermore, IMD 16 may deliver defibrillation pulses to heart 12 via any combination of elongated electrodes 62, 64, 66, and housing electrode 58. Electrodes 58, 62, 64, 66 may also be used to deliver cardioversion pulses to heart 12. Electrodes 62, 64, 66 may be fabricated from any suitable electrically conductive material, such as, but not limited to, platinum, platinum alloy or other materials known to be usable in implantable defibrillation electrodes.

The configuration of system 10 illustrated in FIGS. 1 and 2 is merely one example. In other examples, a system may include epicardial leads and/or patch electrodes instead of or in addition to the transvenous leads 18, 20, 22 illustrated in FIG. 1. Further, IMD 16 need not be implanted within patient 14. In examples in which IMD 16 is not implanted in patient 14, IMD 16 may deliver defibrillation pulses and other therapies to heart 12 via percutaneous leads that extend through the skin of patient 14 to a variety of positions within or outside of heart 12.

Figure 3:
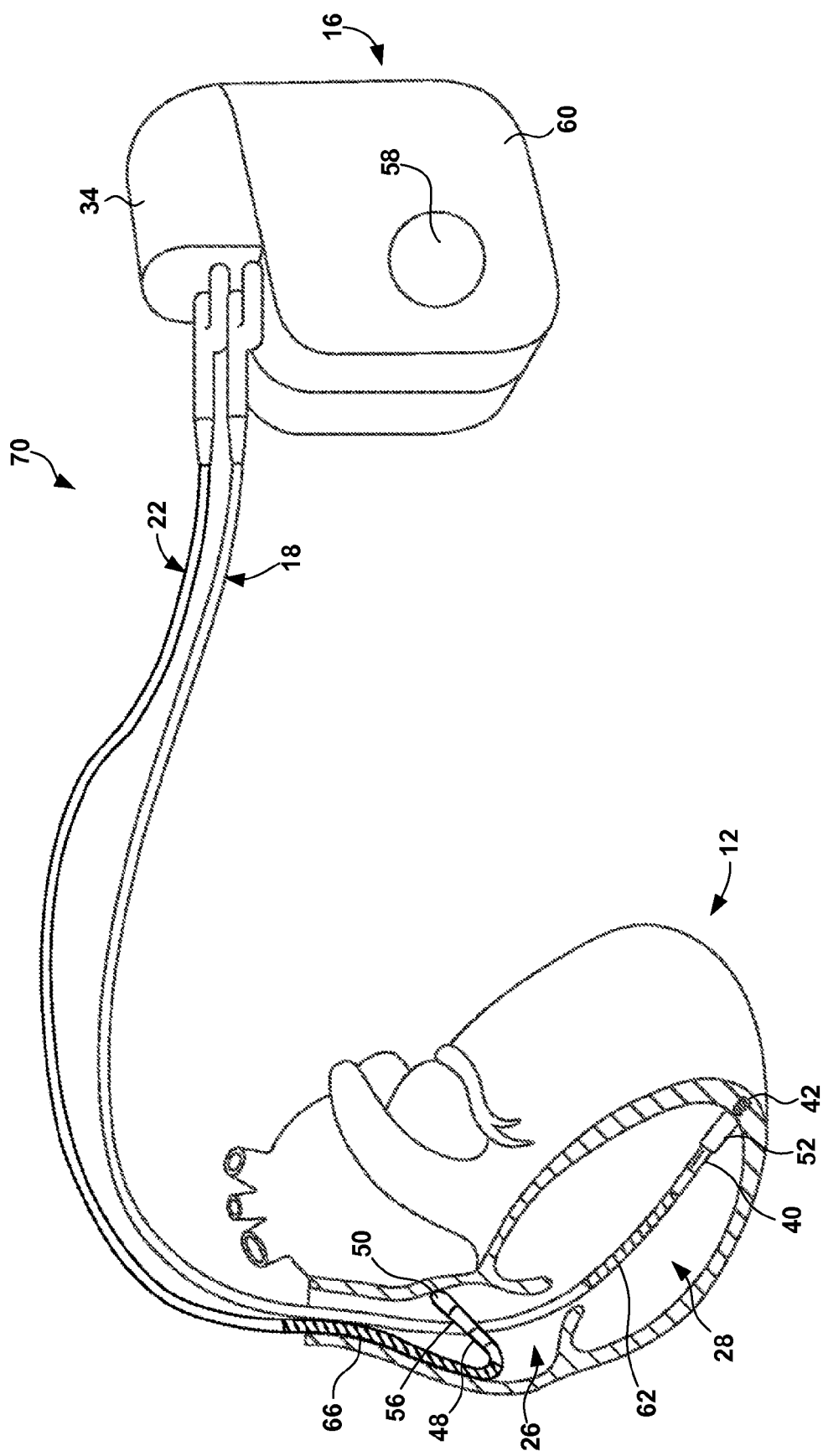
FIG. 3 is a conceptual drawing illustrating the IMD of FIG. 1 coupled to a different configuration of implantable medical leads in conjunction with a heart.

In addition, in other examples, a system may include any suitable number of leads coupled to IMD 16, and each of the leads may extend to any location within or proximate to heart 12. For example, other examples of systems may include three transvenous leads located as illustrated in FIGS. 1 and 2, and an additional lead located within or proximate to left atrium 36. Other examples of systems may include a single lead that extends from IMD 16 into right atrium 26 or right ventricle 28, or two leads that extend into a respective one of the right ventricle 26 and right atrium 26. An example of this type of system is shown in FIG. 3. Any electrodes located on these additional leads may be used in sensing and/or stimulation configurations.

FIG. 3 is a conceptual diagram illustrating another example system 70, which is similar to system 10 of FIGS. 1 and 2, but includes two leads 18, 22, rather than three leads. Leads 18, 22 are implanted within right ventricle 28 and right atrium 26, respectively. System 70 shown in FIG. 3 may be useful for physiological sensing and/or providing pacing, cardioversion, or other therapies to heart 12. AV nodal stimulation and/or other forms of vagal stimulation according to this disclosure may be performed in two lead systems in the manner described herein with respect to three lead systems.

Figure 4:
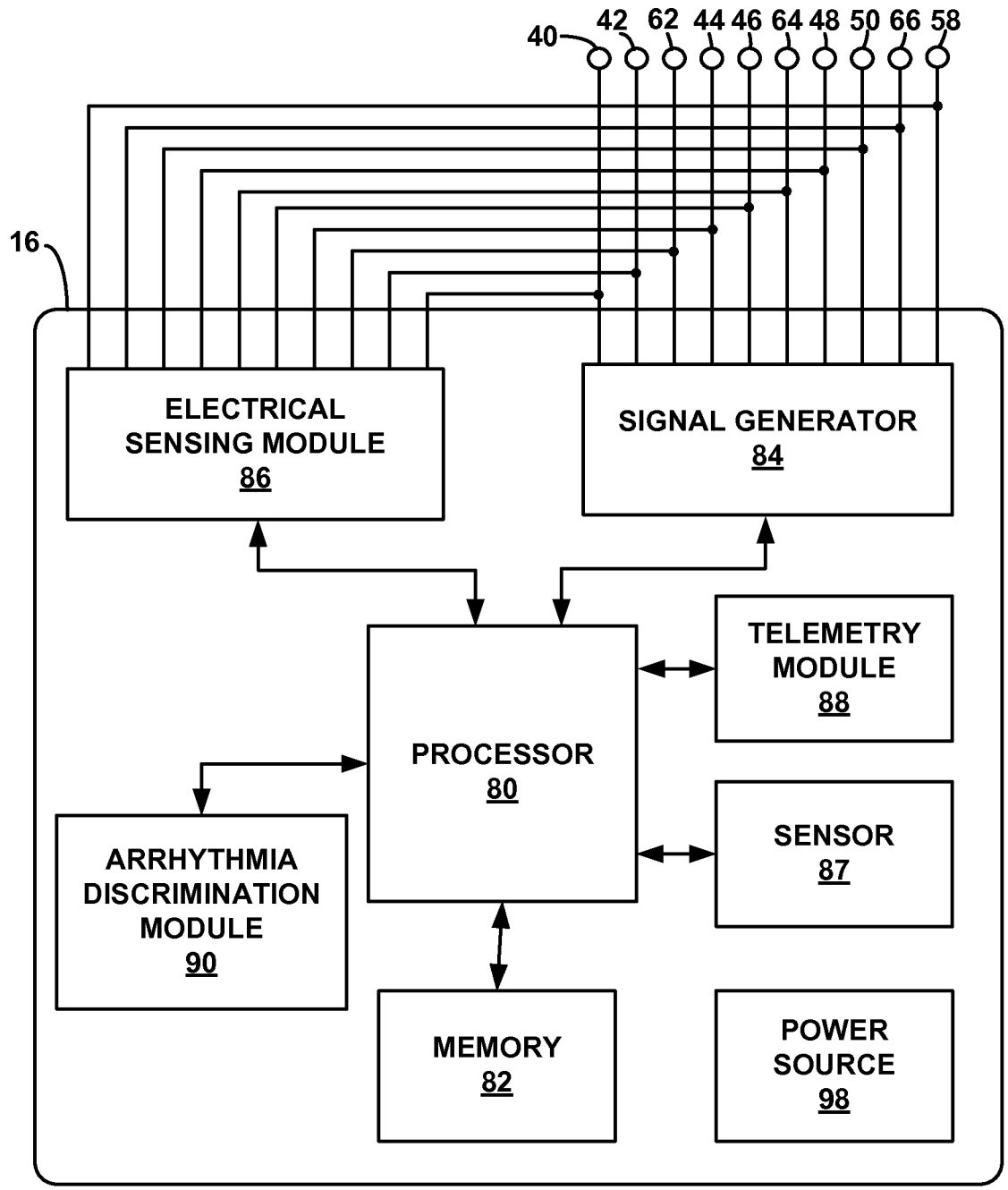
FIG. 4 is a functional block diagram illustrating an example configuration of the IMD of FIG. 1.

FIG. 4 is a functional block diagram illustrating one example configuration of IMD 16. In the example illustrated by FIG. 4, IMD 16 includes a processor 80, memory 82, signal generator 84, electrical sensing module 86, sensor 87, telemetry module 88, and power source 98. Memory 82 may include computer-readable instructions that, when executed by processor 80, cause IMD 16 and processor 80 to perform various functions attributed to IMD 16 and processor 80 herein. Memory 82 may include any volatile, non-volatile, magnetic, optical, or electrical media, such as a random access memory (RAM), read-only memory (ROM), non-volatile RAM (NVRAM), electrically-erasable programmable ROM (EEPROM), flash memory, or any other digital or analog media.

Processor 80 may include any one or more of a microprocessor, a controller, a digital signal processor (DSP), an application specific integrated circuit (ASIC), a field-programmable gate array (FPGA), or equivalent discrete or integrated logic circuitry. In some examples, processor 80 may include multiple components, such as any combination of one or more microprocessors, one or more controllers, one or more DSPs, one or more ASICs, or one or more FPGAs, as well as other discrete or integrated logic circuitry. The functions attributed to processor 80 herein may be embodied as software, firmware, hardware or any combination thereof. IMD 16 also includes an arrhythmia discrimination module 90, as illustrated in FIG. 4, may be implemented by processor 80, e.g., as a hardware component of processor 80, or a software component executed by processor 80.

Processor 80 controls signal generator 84 to deliver stimulation therapy to heart 12 according to operational parameters or programs, which may be stored in memory 82. For example, processor 80 may control stimulation generator 84 to deliver electrical pulses with the amplitudes, pulse widths, frequency, or electrode polarities specified by the selected one or more therapy programs.

Signal generator 84 is electrically coupled to electrodes 40, 42, 44, 46, 48, 50, 58, 62, 64, and 66, e.g., via conductors of the respective lead 18, 20, 22, or, in the case of housing electrode 58, via an electrical conductor disposed within housing 60 of IMD 16. In the illustrated example, signal generator 84 is configured to generate and deliver electrical stimulation therapy to heart 12. For example, signal generator 84 may deliver defibrillation shocks to heart 12 via at least two electrodes 58, 62, 64, 66. Signal generator 84 may deliver pacing pulses via ring electrodes 40, 44, 48 coupled to leads 18, 20, and 22, respectively, and/or helical electrodes 42, 46, and 50 of leads 18, 20, and 22, respectively. Signal generator 84 may also deliver AV nodal vagal stimulation via electrodes 48, 50, and/or 66 of RA lead 22, e.g., in a bipolar configuration or in a unipolar configuration in combination with housing electrode 58. In some examples, signal generator 84 delivers one or more of these types of stimulation in the form of electrical pulses. In other examples, signal generator 84 may deliver one or more of these types of stimulation in the form of other signals, such as sine waves, square waves, or other substantially continuous time signals.

In some examples, signal generator 84 is configured to deliver AV nodal vagal stimulation in the form of a series of high frequency pulses. For example, signal generator 84 may deliver AV nodal vagal stimulation, e.g., via electrodes 48, 50, and/or 66 of RA lead 22, in a burst pattern characterized by a plurality of pulse trains of high frequency pulses or as a continuous train of pulses. High frequency stimulation may be particularly effective in interrupting the conduction of cardiac impulses across the AV node, e.g., from the atria to the ventricles, which may be particularly helpful for distinguishing between SVT and VT.

Signal generator 84 may include a switch module and processor 80 may use the switch module to select, e.g., via a data/address bus, which of the available electrodes are used to deliver stimulation signals, e.g., defibrillation, pacing, and/or AV nodal vagal stimulation signals. The switch module may include a switch array, switch matrix, multiplexer, or any other type of switching device suitable to selectively couple a signal to selected electrodes.

Electrical sensing module 86 monitors signals from at least one of electrodes 40, 42, 44, 46, 48, 50, 58, 62, 64 or 66 in order to monitor electrical activity of heart 12. Electrical sensing module 86 may also include a switch module to select which of the available electrodes are used to sense the heart activity. In some examples, processor 80 may select the electrodes that function as sense electrodes, i.e., select the sensing configuration, via the switch module within electrical sensing module 86, e.g., by providing signals via a data/address bus.

In some examples, electrical sensing module 86 includes multiple detection channels, each of which may comprise an amplifier. Each sensing channel may detect electrical activity in respective chamber of heart 12, and may be configured to detect either R-waves or P-waves. In some examples, electrical sensing module 86 or processor 80 may include an analog-to-digital converter for digitizing the signal received from a sensing channel for electrogram (EGM) signal processing by processor 80. In response to the signals from processor 80, the switch module within electrical sensing module 86 may couple the outputs from the selected electrodes to one of the detection channels or the analog-to-digital converter.

During pacing, escape interval counters maintained by processor 80 may be reset upon sensing of R-waves and P-waves with respective detection channels of electrical sensing module 86. Signal generator 84 may include pacer output circuits that are coupled, e.g., selectively by a switching module, to any combination of electrodes 40, 42, 44, 46, 48, 50, 58, 62, or 66 appropriate for delivery of a bipolar or unipolar pacing pulse to one or more of the chambers of heart 12. Processor 80 may control signal generator to deliver a pacing pulse to a chamber upon expiration of an escape interval. Processor 80 may reset the escape interval counters upon the generation of pacing pulses by stimulation generator 84, or detection of an intrinsic depolarization in a chamber, and thereby control the basic timing of cardiac pacing functions. The escape interval counters may include P-P, V-V, RV-LV, A-V, A-RV, or A-LV interval counters, as examples. The value of the count present in the escape interval counters when reset by sensed R-waves and P-waves may be used by processor 80 to measure the durations of R-R intervals, P-P intervals, P-R intervals and R-P intervals.

Processor 80 may use the count in the interval counters to detect heart rate, such as an atrial rate or ventricular rate. Processor 80 may also use the count in the interval counters to detect a high cardiac rate, such as a tachycardia event. In response to the detected high cardiac rate, arrhythmia discrimination module 90 may control signal generator 84 to deliver AV nodal vagal stimulation as described herein. In some examples, processor 80 maintains an event counter. In response to detecting a high cardiac rate, processor 80 may increment the event counter. Arrhythmia discrimination module 90 may control signal generator 84 to deliver AV nodal vagal stimulation when the event counter exceeds a threshold value. In addition, arrhythmia discrimination module 90 may classify the high cardiac rate as SVT or VT based on a physiological parameter sensed during or subsequent to signal generator 84 delivering the AV nodal vagal stimulation. In some examples, arrhythmia discrimination module 90 may further distinguish between atrial fibrillation and tachycardia as well as between ventricular fibrillation and tachycardia, e.g., based on a count in an interval counter and/or a parameter sensed during or subsequent to AV nodal vagal stimulation.

Processor 80 may also derive other physiological parameters from signals sensed via electrical sensing module 86. For example, processor 80 may establish one or more indicators of ejection fraction and/or heart failure status from electrical signals sensed via electrical sensing module 86. In particular, impedance signals may be used to determine flow or pressure, which may indicate ejection fraction and/or heart failure status.

IMD 16 may also include one or more sensors 87 separate from electrodes 40, 42, 44, 46, 48, 50, 58, 62, 64 and 66. Via a signal generated by sensor 87, processor 80 may monitor one or more physiological parameters indicative of cardiac contraction, autonomic tone, heart failure, and/or ejection fraction. Examples of sensors 87 that may generate a signal indicative of cardiac contraction include a intracardiac or intravascular pressure sensor, an accelerometer or other sensor capable of detecting heart or blood sounds, vibrations, or motion, an optical or ultrasonic sensor capable or detecting changes in flow associated with cardiac contractions, or an optical sensor capable of detecting oxygen saturation or tissue perfusion changes associated with cardiac contractions. Processor 80 may detect cardiac contractions based on signals from one or more sensors 87, and detect arrhythmias based on the detected cardiac contractions.

Processor 80 may also detect one or more hemodynamic parameters via one or more sensors 87. For example, sensors 87 may monitor blood pressure in one or more of right ventricle 28, left ventricle 32, another chamber of heart 12, and an artery of patient 14. As one example, one or more of sensors 87 may monitor blood pressure within a pulmonary artery of patient 14. As described with further detail with respect to FIG. 9, arrhythmia discrimination module 90 may utilize blood pressure values to facilitate classification of a detected high cardiac rate as SVT or VT.

In some examples, memory 82 may store waveform templates that arrhythmia discrimination module 90 may access to facilitate classification of a detected high cardiac rate as SVT or VT. The templates may represent known SVT rhythms, e.g., sinus tachycardia or atrial fibrillation, experienced by patient 14. In some examples, memory 82 may also store templates representative of known VT rhythms, e.g., ventricular fibrillation or ventricular tachycardia, experienced by patient 14. As described with further detail with respect to FIG. 8, arrhythmia discrimination module 90 may compare one or more signal characteristic of a signal indicative of cardiac contractions to the templates stored in memory 82 to classify a rhythm as SVT or VT.

Telemetry module 88 includes any suitable hardware, firmware, software or any combination thereof for communicating with another device, such as programmer 24 (FIG. 1). Under the control of processor 80, telemetry module 88 may receive downlink telemetry from and send uplink telemetry to programmer 24 with the aid of an antenna, which may be internal and/or external. Processor 80 may provide the data to be uplinked to programmer 24 and receive downlinked data from programmer 24 via an address/data bus. In some examples, telemetry module 88 may provide received data to processor 80 via a multiplexer.

In some examples, processor 80 transmits indications of detected tachycardias via telemetry module 88. Processor 80 may also transmit an indication that a tachycardia was classified as a SVT via telemetry module 80. The indication may include a notification that a therapy, e.g., defibrillation and/or cardioversion, was not delivered to the ventricles of patient 14 based on the SVT classification. This may be particularly important if processor 80 withholds or modifies a therapy, e.g., withholds cardioversion, defibrillation and/or anti-tachycardia pacing (ATP), based on classification of a tachycardia as SVT. The indication may include information that would allow a user to confirm that a therapy was properly withheld or modified instead of altered due to integrity issues associated with IMD 16 and/or another component of therapy system 10. Processor 80 may also transmit, via telemetry module 88, information regarding AV nodal vagal stimulation delivered by signal generator 84 and a response to AV nodal vagal stimulation, e.g., detected by electrical sensing module 86.

Figure 5:
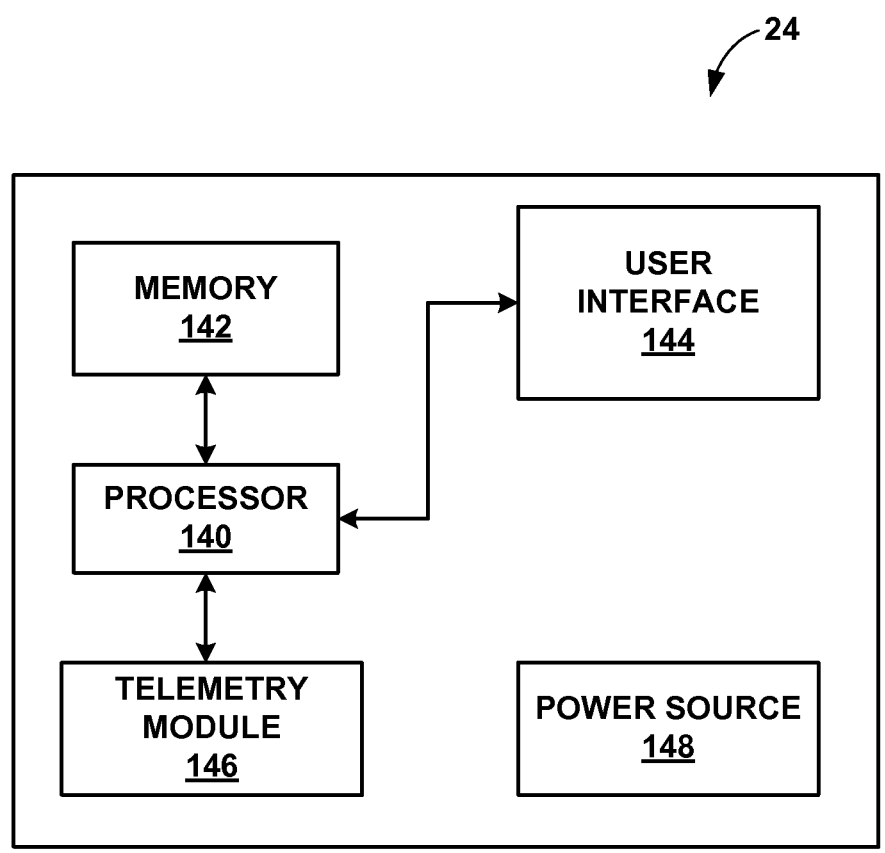
FIG. 5 is block diagram of an example external programmer that facilitates user communication with the IMD.

FIG. 5 is a functional block diagram of an example configuration of programmer 24. As shown in FIG. 5, programmer 24 includes processor 140, memory 142, user interface 144, telemetry module 146, and power source 148. Programmer 24 may be a dedicated hardware device with dedicated software for programming of IMD 16. Alternatively, programmer 24 may be an off-the-shelf computing device running an application that enables programmer 24 to program IMD 16.

A user may use programmer 24 to select therapy programs (e.g., sets of stimulation parameters), generate new therapy programs, or modify therapy programs for IMD 16. The clinician may interact with programmer 24 via user interface 144, which may include a display to present a graphical user interface to a user, and a keypad or another mechanism for receiving input from a user.

Processor 14 can take the form one or more microprocessors, DSPs, ASICs, FPGAs, programmable logic circuitry, or the like, and the functions attributed to processor 102 herein may be embodied as hardware, firmware, software or any combination thereof. Memory 142 may store instructions that cause processor 140 to provide the functionality ascribed to programmer 24 herein, and information used by processor 140 to provide the functionality ascribed to programmer 24 herein. Memory 142 may include any fixed or removable magnetic, optical, or electrical media, such as RAM, ROM, CD-ROM, hard or floppy magnetic disks, EEPROM, or the like. Memory 142 may also include a removable memory portion that may be used to provide memory updates or increases in memory capacities. A removable memory may also allow patient data to be easily transferred to another computing device, or to be removed before programmer 24 is used to program therapy for another patient. Memory 142 may also store information that controls therapy delivery by IMD 16, such as stimulation parameter values.

Programmer 24 may communicate wirelessly with IMD 16, such as using RF communication or proximal inductive interaction. This wireless communication is possible through the use of telemetry module 146, which may be coupled to an internal antenna or an external antenna. An external antenna that is coupled to programmer 24 may correspond to the programming head that may be placed over heart 12, as described above with reference to FIG. 1. Telemetry module 146 may be similar to telemetry module 88 of IMD 16 (FIG. 4).

Telemetry module 146 may also be configured to communicate with another computing device via wireless communication techniques, or direct communication through a wired connection. Examples of local wireless communication techniques that may be employed to facilitate communication between programmer 24 and another computing device include RF communication according to the 802.11 or Bluetooth specification sets, infrared communication, e.g., according to the IrDA standard, or other standard or proprietary telemetry protocols. In this manner, other external devices may be capable of communicating with programmer 24 without needing to establish a secure wireless connection. An additional computing device in communication with programmer 24 may be a networked device such as a server capable of processing information retrieved from IMD 16.

In some examples, processor 140 of programmer 24 and/or one or more processors of one or more networked computers may perform all or a portion of the techniques described herein with respect to processor 80 and IMD 16. For example, processor 140 or another processor may receive indications of cardiac depolarizations or contractions, a signal from one or more sensors 87, or information regarding detected tachycardias from IMD 16 via telemetry module 146. In some examples, processor 140 may initiate or modify AV nodal vagal stimulation and/or classify a tachycardia as SVT or VT based on information sensed during or subsequent to the AV nodal vagal stimulation, as described herein with respect to IMD 16 and processor 80. In some examples, processor 140 may include or implement an arrhythmia discrimination module 90 to perform the techniques described herein with respect to arrhythmia discrimination module 90.

Figure 6:
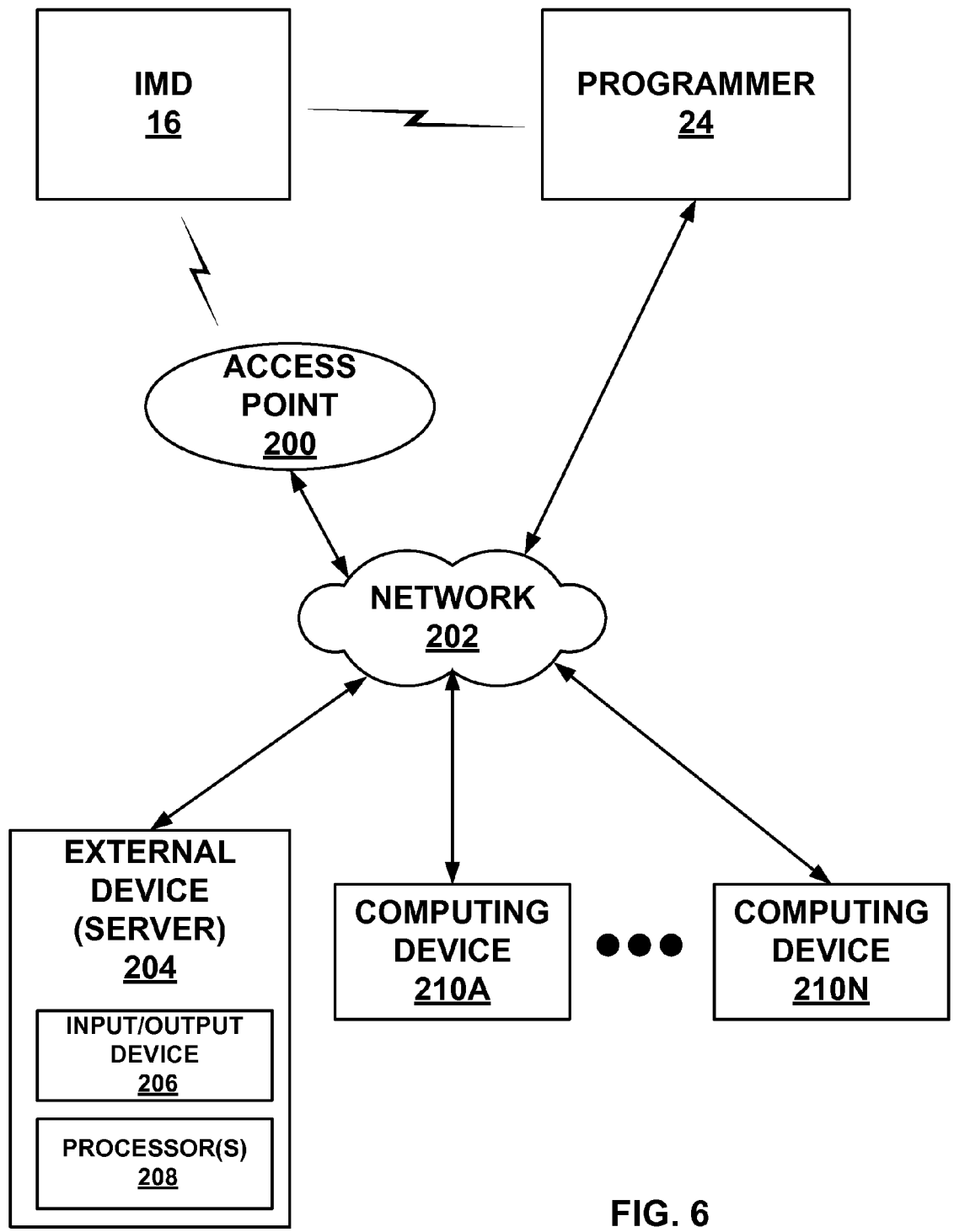
FIG. 6 is a block diagram illustrating an example system that includes an external device, such as a server, and one or more computing devices that are coupled to the IMD and programmer shown in FIG. 1 via a network.

FIG. 6 is a block diagram illustrating an example system that includes an external device, such as a server 204, and one or more computing devices 210A-210N, that are coupled to the IMD 16 and programmer 24 shown in FIG. 1 via a network 202. In this example, IMD 16 may use its telemetry module 88 to communicate with programmer 24 via a first wireless connection, and to communication with an access point 200 via a second wireless connection. In the example of FIG. 6, access point 200, programmer 24, server 204, and computing devices 210A-210N are interconnected, and able to communicate with each other, through network 202. In some cases, one or more of access point 200, programmer 24, server 204, and computing devices 210A-210N may be coupled to network 202 through one or more wireless connections. IMD 16, programmer 24, server 204, and computing devices 210A-210N may each comprise one or more processors, such as one or more microprocessors, DSPs, ASICs, FPGAs, programmable logic circuitry, or the like, that may perform various functions and operations, such as those described herein.

Access point 200 may comprise a device that connects to network 202 via any of a variety of connections, such as telephone dial-up, digital subscriber line (DSL), or cable modem connections. In other examples, access point 200 may be coupled to network 202 through different forms of connections, including wired or wireless connections. In some examples, access point 200 may be co-located with patient 14 and may comprise one or more programming units and/or computing devices (e.g., one or more monitoring units) that may perform various functions and operations described herein. For example, access point 200 may include a home-monitoring unit that is co-located with patient 14 and that may monitor the activity of IMD 16. In some examples, server 204 or computing devices 210 may control or perform any of the various functions or operations described herein, e.g., include or implement an arrhythmia discrimination module 90 and/or initiate or modify AV nodal vagal stimulation.

In some cases, server 204 may be configured to provide a secure storage site for data that has been collected from IMD 16 and/or programmer 24. Network 202 may comprise a local area network, wide area network, or global network, such as the Internet. In some cases, programmer 24 or server 206 may assemble data in web pages or other documents for viewing by trained professionals, such as clinicians, via viewing terminals associated with computing devices 210A-210N. The illustrated system of FIG. 6 may be implemented, in some aspects, with general network technology and functionality similar to that provided by the Medtronic CARELINK® Network developed by Medtronic, Inc., of Minneapolis, Minn.

In some examples, processor 208 of server 204 may be configured to provide some or all of the functionality ascribed to processor 80 of IMD 16 herein. For example, processor 206 may receive indications of cardiac depolarizations or contractions, a signal from one or more sensors 87, or information regarding detected tachycardias from IMD via access point 200 or programmer 24 and network 202. Processor 206 may also may initiate or modify AV nodal vagal stimulation and/or classify a tachycardia as SVT or VT based on information sensed during or subsequent to the AV nodal vagal stimulation. In some examples, server 204 relays received indications of cardiac depolarizations or contractions, a signal from one or more sensors 87, or information regarding detected tachycardias and parameters sensed during or subsequent to AV nodal vagal stimulation provided by one or more of IMD 16 or programmer 24 to one or more of computing devices 210 via network 202. A processor of a computing device 210 may provide some or all of the functionality ascribed to processor 80 of IMD 16 herein. In some examples, a processor of computing device 210 may include or implement an arrhythmia discrimination module 90 to perform the techniques described herein with respect to arrhythmia discrimination module 90.

Figure 7:
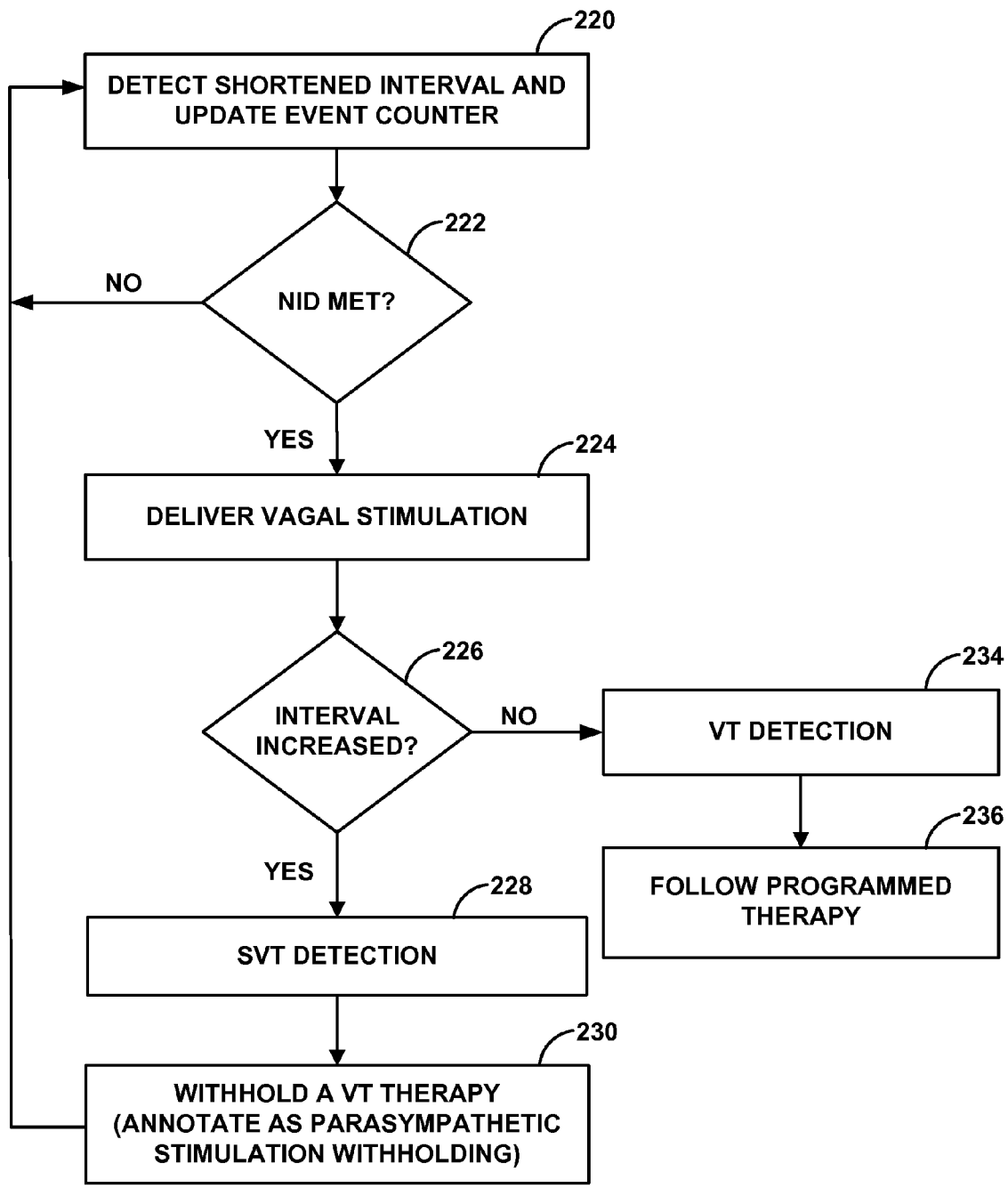
FIG. 7 is a flow diagram of an example method of classifying a high cardiac rate as supraventricular tachycardia (SVT) or ventricular tachycardia (VT).

FIG. 7 is a flow diagram of an example method of classifying a high cardiac rate as SVT or VT. The example method of FIG. 7 is described as being performed by processor 80 and arrhythmia discrimination module 90 of IMD 16. In other examples, one or more other processors of one or more other devices may implement all or part of this method, e.g., may include or implement arrhythmia discrimination module 90.

Processor 80 may detect a shortened cardiac interval and update an event counter (220). For example, as described with respect to FIG. 4, processor 80 may use interval counters to detect heart rate, such as an atrial or ventricular rate. A shortened interval, e.g., P-P, V-V, RV-LV, A-V, A-RV, or A-LV interval, may indicate a high cardiac rate. Processor 80 may determine whether a number of intervals to detect (NID) threshold for detecting tachycardia has been met (222). If not, processor 80 continues to monitor cardiac intervals until the NID threshold is met. As one example, the NID threshold may require a specified number of shortened intervals within a predetermined period of time.

When the NID threshold for detecting tachycardia has been met, arrhythmia discrimination module 90 controls signal generator 84 to deliver vagal stimulation, e.g., AV nodal vagal stimulation (224). In other examples, arrhythmia discrimination module 90 may control signal generator 84 to deliver vagal stimulation after different criteria is met, e.g., after detecting a fewer number of shortened intervals, and may not require the NID criteria to be met before delivering vagal stimulation. In some examples, signal generator 84 may deliver vagal stimulation during the atrial refractory period to avoid induction of SVT.

During or subsequent to the vagal stimulation, arrhythmia discrimination module 90 may determine whether a cardiac interval increased (226). If a cardiac interval increased relative to the interval value prior to vagal stimulation, arrhythmia discrimination module 90 may classify the rhythm as SVT (228). Since the vagus nerve innervates the AV node, vagal stimulation may block atrial signals from propagating to the ventricles. An increase in a cardiac interval, e.g., a R-R interval indicative of ventricular rate, during or subsequent to vagal stimulation may be indicative of SVT as the tachycardia from the atria is prevented from propagating to the ventricles.

In response to the classification of the tachycardia as SVT, processor 80 may control signal generator 84 to withhold delivery of therapy to the ventricles, such as cardioversion and/or defibrillation therapy, and provide an indication to a user, e.g., via telemetry module 88, that SVT was detected and/or delivery of therapy to the ventricles has been withheld (230). If processor 80 withholds or modifies therapy e.g., withholds cardioversion, defibrillation, and/or anti-tachycardia pacing, based on classifying a tachycardia as SVT, processor 80 may provide an indication that would allow a user to confirm that a therapy was properly withheld or modified instead of altered due to integrity issues associated with IMD 16 and/or another component of therapy system 10.

If a cardiac interval after vagal stimulation did not increase relative to the interval value prior to vagal stimulation, arrhythmia discrimination module 90 may classify the rhythm as VT (234). Processor 80 may control signal generator 84 to deliver a programmed therapy, e.g., a defibrillation and/or cardioversion therapy (236).

Figure 8:
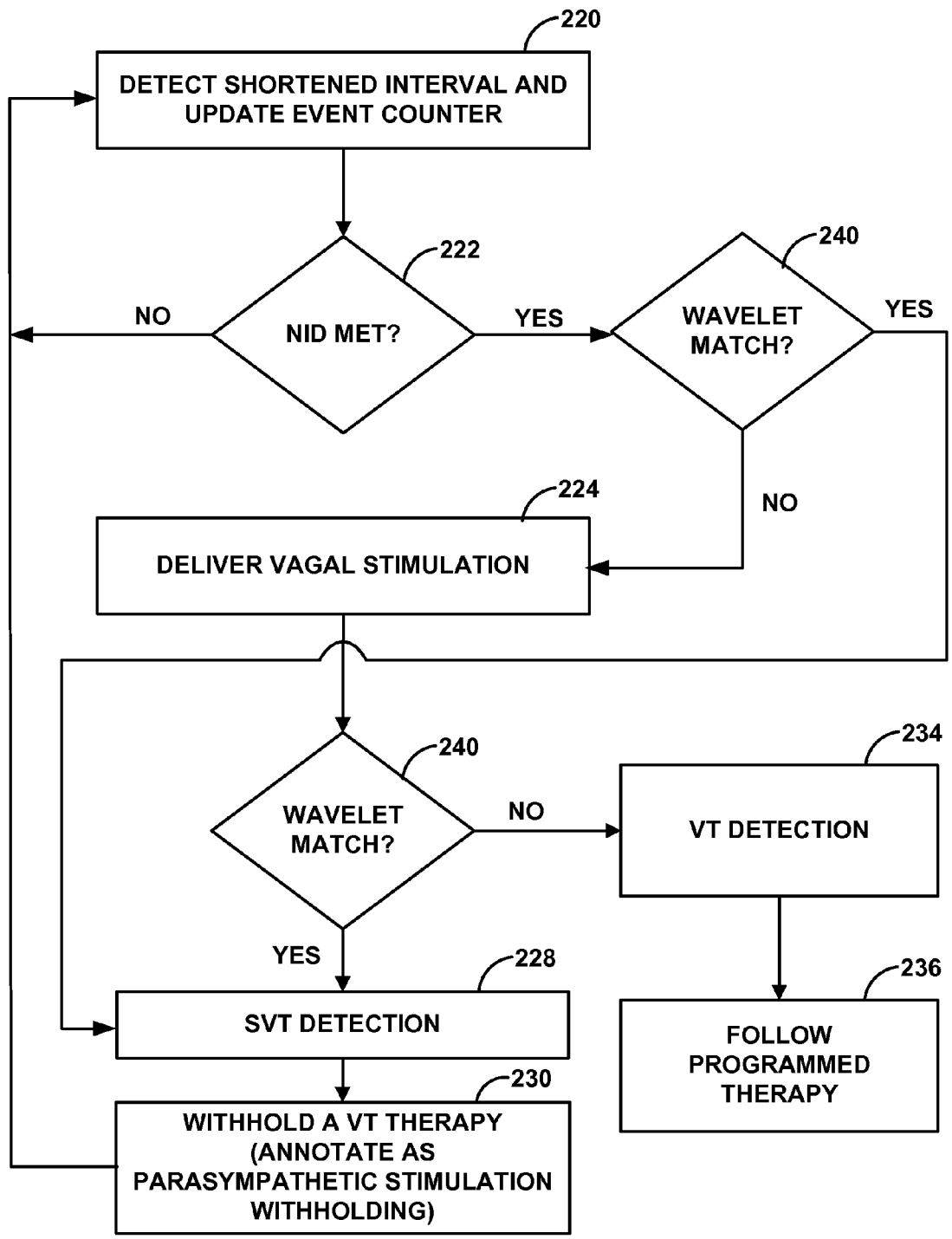
FIG. 8 is a flow diagram of another example method of classifying a high cardiac rate as SVT or VT.

FIG. 8 is a flow diagram of another example method of classifying a high cardiac rate as SVT or VT. The example method of FIG. 8 is described as being performed by processor 80 and arrhythmia discrimination module 90 of IMD 16. In other examples, one or more other processors of one or more other devices may implement all or part of this method, e.g., may include or implement arrhythmia discrimination module 90. In some examples, processor 80 may deliver anti-tachycardia pacing (ATP) in response to the detection of VT (234). In such examples, processor 80 may provide an indication to a user, e.g., via telemetry module 88, that ATP was delivered in response to the VT detection.

As described with respect to FIG. 7, processor 80 may detect a shortened cardiac interval and update an event counter (220). Processor 80 may also determine whether a number of intervals to detect (NID) threshold for detecting tachycardia has been met (222). If not, processor 80 may continue to monitor cardiac intervals until the NID threshold is met.

When the NID threshold for detecting tachycardia has been met, arrhythmia discrimination module 90 may determine whether at least one waveform characteristic of a signal indicative of cardiac depolarization matches a template (240). For example, arrhythmia discrimination module 90 may compare one or more waveform characteristics, e.g., peak, morphology, of an electrogram (EGM) signal sensed by sensing module 86 to a plurality of templates, e.g., stored in memory 82. The templates may represent known SVT rhythms, e.g., sinus tachycardia, atrial fibrillation, experienced by patient 14. If the signal does match a template wavelet, arrhythmia discrimination module 90 may classify the rhythm as SVT (228). In some examples, arrhythmia discrimination module 90 may use other techniques to differentiate VT from SVT based on one or more waveform characteristic. For example, arrhythmia discrimination module 90 may classify the rhythm as SVT if the width of the QRS complex is less than a threshold and/or classify the rhythm as VT if the width of the QRS complex is greater than a threshold.

In some examples, arrhythmia discrimination module 90 may also compare one or more waveform characteristic of the cardiac signal to wavelet templates that represent known VT rhythms, e.g., ventricular tachycardia or ventricular fibrillation, experienced by patient 14 and classify the rhythm as VT based on the comparison. However, in other examples, arrhythmia discrimination module 90 may only compare one or more waveform characteristic of the cardiac signal to wavelet templates that represent known SVT rhythms, e.g., sinus tachycardia, atrial fibrillation, experienced by patient 14. In some examples, arrhythmia discrimination module 90 may perform template matching after different criteria is met, e.g., after detecting a fewer number of shortened intervals, and may not require the NID criteria to be met before performing template matching.

If the signal does not match a template wavelet, arrhythmia discrimination module 90 controls signal generator 82 to deliver vagal stimulation, e.g., AV nodal vagal stimulation (224). During or subsequent to delivering vagal stimulation, arrhythmia discrimination module 90 may again determine whether at least one waveform characteristic of a signal indicative of cardiac depolarization matches a template (240). Since the vagus nerve innervates the AV node, vagal stimulation may block atrial signals from propagating to the ventricles. This may allow arrhythmia discrimination module 90 to more easily match some SVTs to stored template wavelets during or subsequent to vagal stimulation. If the signal does match a template wavelet, processor 80 may classify the rhythm as SVT (228). Arrhythmia discrimination module 90 may also used values of cardiac intervals to classify a rhythm as SVT, as described with respect to FIG. 7, in combination with template matching.

As described in further detail with respect to FIG. 7, in response to the classification of the tachycardia as SVT, processor 80 may control signal generator 84 to withhold delivery of therapy to the ventricles, such as cardioversion, ATP, and/or defibrillation therapy, and provide an indication to a user, e.g., via telemetry module 88, that SVT was detected and/or delivery of therapy to the ventricles has been withheld (230).

If the cardiac signal does not match a template wavelet, arrhythmia discrimination module 90 may classify the rhythm as VT (234) and processor 80 may control signal generator 84 to deliver a programmed therapy, e.g., a defibrillation and/or cardioversion therapy (236). Cardiac interval values prior and during or subsequent to vagal stimulation, as described with respect to FIG. 7, may be used in combination with template matching to confirm that the classification of VT.

Figure 9:
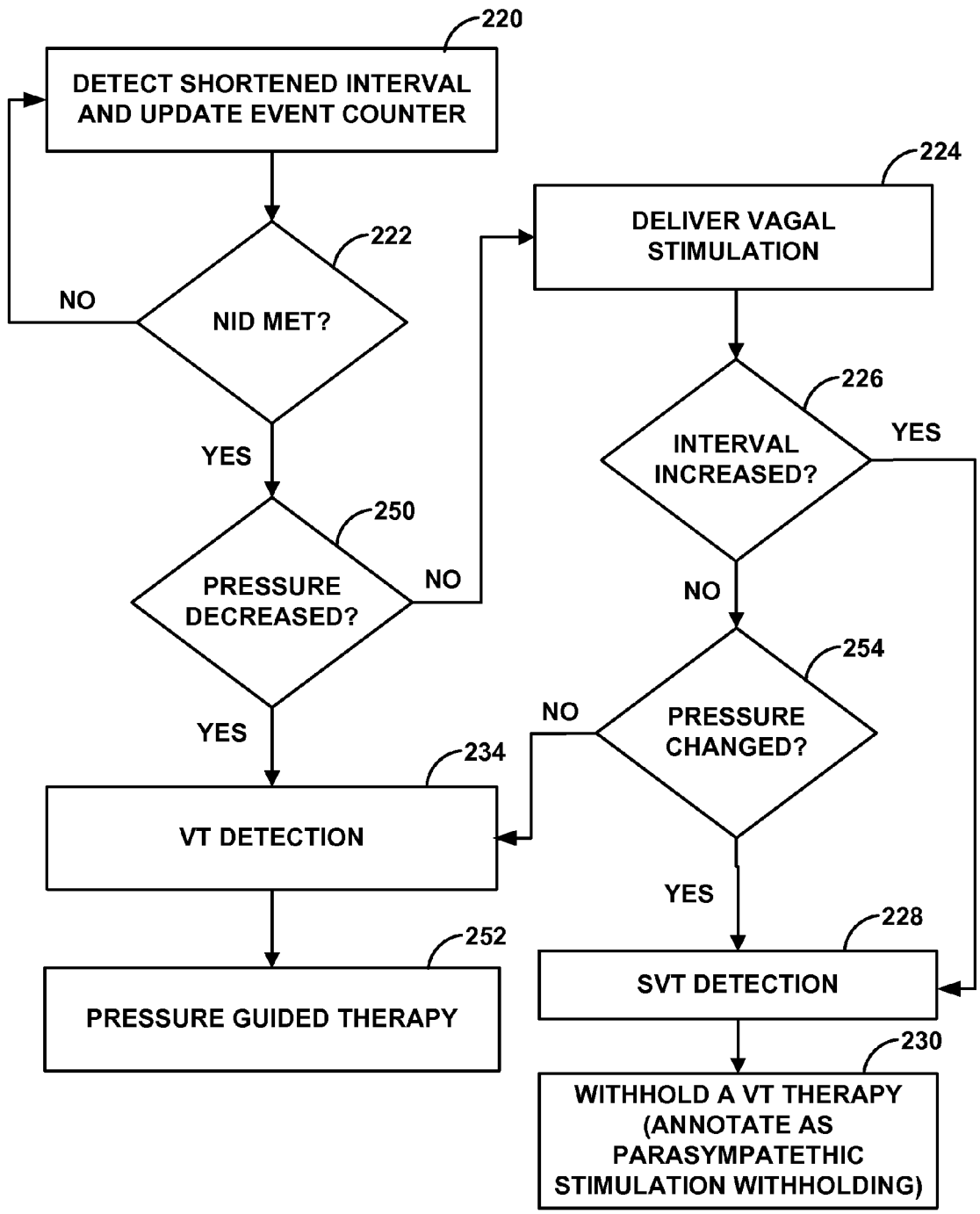
FIG. 9 is a flow diagram of another example method of classifying a high cardiac rate as SVT or VT.

FIG. 9 is a flow diagram of another example method of classifying a high cardiac rate as SVT or VT. The example method of FIG. 9 is described as being performed by processor 80 and arrhythmia discrimination module 90 of IMD 16. In other examples, one or more other processors of one or more other devices may implement all or part of this method, e.g., may include or implement arrhythmia discrimination module 90.

As described with respect to FIG. 7, processor 80 may detect a shortened cardiac interval and update an event counter (220). Processor 80 may also determine whether a number of intervals to detect (NID) threshold for detecting tachycardia has been met (222). If not, processor 80 may continue to monitor cardiac intervals until the NID threshold is met.

When the NID threshold for detecting tachycardia has been met, arrhythmia discrimination module 90 determines whether a blood pressure or other hemodynamic characteristic has decreased (250). For example, arrhythmia discrimination module 90 may determine whether the blood pressure, e.g., in one or more of right ventricle 28, left ventricle 32, another chamber of heart 12, and/or an artery of patient 14, has decreased below a threshold value, e.g., approaching zero. As VT rhythms may compromise pumping efficiency more than SVT rhythms, arrhythmia discrimination module 90 may classify a tachycardia as VT if it is accompanied by a significant decrease in blood pressure (234).

In some examples, arrhythmia discrimination module 90 may evaluate the hemodynamic characteristic after different criteria is met, e.g., after detecting a fewer number of shortened intervals, and may not require the NID criteria to be met before evaluating the hemodynamic characteristic.

If the hemodynamic performance is not decreased significantly enough for arrhythmia discrimination module 90 to characterize the tachycardia as VT, arrhythmia discrimination module 90 controls signal generator 84 to deliver vagal stimulation, e.g., AV nodal vagal stimulation (224). During or subsequent to the vagal stimulation, arrhythmia discrimination module 90 may determine whether a cardiac interval increased (226). If a cardiac interval value increased relative to the interval value prior to vagal stimulation, processor 80 may classify the rhythm as SVT (228).

If a cardiac interval value is not increased relative to the interval value prior to vagal stimulation, arrhythmia discrimination module 90 may determine whether a blood pressure or other hemodynamic characteristic has changed relative to a value obtained prior to vagal stimulation (254). In some examples, vagal stimulation may not alter the values of cardiac intervals in the presence of SVT but may impact hemodynamic characteristics. For example, vagal stimulation may result in a decrease in blood pressure that may be propagated to the ventricles when a SVT is present.

If arrhythmia discrimination module 90 determines that the blood pressure has decreased relative to a value obtained prior to vagal stimulation, arrhythmia discrimination module 90 may classify the tachycardia as SVT (228). In response to the classification of the tachycardia as SVT, processor 80 may control signal generator 84 to withhold delivery of therapy to the ventricles, such as cardioversion and/or defibrillation therapy, and provide an indication to a user, e.g., via telemetry module 88, that SVT was detected and/or delivery of therapy to the ventricles has been withheld (230).

If arrhythmia discrimination module 90 determines that the blood pressure has not decreased relative to a value obtained prior to vagal stimulation, arrhythmia discrimination module 90 may classify the rhythm as VT (234). Processor 80 may control signal generator 84 to deliver a programmed therapy, e.g., a defibrillation, ATP, and/or cardioversion therapy, in response to the classification of the arrhythmia as VT (252). In some examples, processor 80 monitors blood pressure to titrate the therapy.

In some examples, arrhythmia discrimination module 90 may use wavelet template matching, as described with respect to FIG. 8, in combination with monitoring hemodynamic response to classify a rhythm as SVT or VT. In other examples, arrhythmia discrimination module 90 may utilize values of one or more hemodynamic characteristic to classify a rhythm as SVT or VT without the use of cardiac intervals.

Various examples of the invention have been described. These and other examples are within the scope of the following claims.

The invention claimed is:

1. A method comprising:
    detecting a tachycardia based on at least one value of a cardiac interval;
    delivering vagal stimulation in response to the detection of the tachycardia;
    sensing a physiological parameter other than the cardiac interval during or subsequent to delivering the vagal stimulation; and
    classifying the tachycardia as supraventricular or ventricular based on the sensed physiological parameter.

2. The method of claim 1, wherein classifying the tachycardia comprises classifying the tachycardia as supraventricular based on the sensed physiological parameter, the method further comprising providing an indication to a user based on the classification of supraventricular tachycardia.

3. The method of claim 1, wherein classifying the tachycardia comprises classifying the tachycardia as supraventricular based on the sensed physiological parameter, the method further comprising withholding a defibrillation therapy based on the classification of supraventricular tachycardia.

4. The method of claim 1, further comprising comparing at least one waveform characteristic of a signal indicative of a cardiac depolarization and corresponding to the tachycardia to a template, wherein delivering vagal stimulation comprises delivering the vagal stimulation based on the comparison.

5. The method of claim 1,
    wherein the sensed physiological parameter comprises at least one waveform characteristic of a signal indicative of a cardiac depolarization,
    the method further comprising comparing the at least one waveform characteristic to a template, and
    wherein classifying the tachycardia comprises classifying the tachycardia as supraventricular or ventricular based on the comparison.

6. The method of claim 1, further comprising determining a value of a blood pressure of the patient, wherein delivering vagal stimulation comprises delivering the vagal stimulation based on the blood pressure value.

7. The method of claim 1, wherein sensing the physiological parameter comprises sensing a value of a blood pressure of the patient, and wherein classifying the tachycardia comprises classifying the tachycardia based on the value of the blood pressure of the patient.

8. The method of claim 7, wherein sensing the value of the blood pressure comprises sensing blood pressure within at least one of a chamber of a heart or an artery of the patient.

9. The method of claim 7, wherein sensing the value of the blood pressure comprises sensing blood pressure within a right ventricle of the patient.

10. The method of claim 1, wherein delivering vagal stimulation comprises delivering the vagal stimulation to at least one of a sinoatrial node fat pad or an atrioventricular node fat pad of the patient.

11. The method of claim 1, wherein delivering vagal stimulation comprises delivering the vagal stimulation to a cardiac branch of a vagus nerve of the patient.

12. The method of claim 1, wherein delivering vagal stimulation comprises delivering at least one of delivering the vagal stimulation intracardially or epicardially.

13. A system comprising:
    a stimulation generator configured to deliver vagal stimulation to a patient;
    a processor configured to detect a tachycardia based on at least one value of a cardiac interval; and
    an arrhythmia discrimination module configured to control the stimulation generator to deliver the vagal stimulation in response to the detection of the tachycardia, detect a physiological parameter other than the cardiac interval during or subsequent to the stimulation generator delivering the vagal stimulation, and classify the tachycardia as supraventricular or ventricular based on the detected physiological parameter.

14. The system of claim 13, further comprising a user interface configured to provide an indication in response to the arrhythmia discrimination module classifying the tachycardia as supraventricular.

15. The system of claim 14, further comprising at least one of a programmer comprising the user interface or a computing device comprising the user interface.

16. The system of claim 13, wherein the processor is configured to control the stimulation generator to withhold a defibrillation therapy in response to the classification of the tachycardia as supraventricular.

17. The system of claim 13, wherein the arrhythmia discrimination module is configured to compare at least one waveform characteristic of a signal indicative of cardiac depolarization and corresponding to the tachycardia to a template and control the stimulation generator to deliver the vagal stimulation based on the comparison.

18. The system of claim 13, wherein the detected physiological parameter comprises at least one waveform characteristic of a signal indicative of a cardiac depolarization, wherein the arrhythmia discrimination module is configured to compare the at least one waveform characteristic to a template and classify the tachycardia as supraventricular or ventricular based on the comparison.

19. The system of claim 13, wherein the arrhythmia discrimination module is configured to detect a value of a blood pressure of the patient and control the stimulation generator to deliver the vagal stimulation based on the blood pressure value.

20. The system of claim 13, wherein the physiological parameter comprises a value of a blood pressure of the patient, and wherein the arrhythmia discrimination module is configured to classify the tachycardia based on the value of the blood pressure of the patient.

21. The system of claim 20, further comprising a sensor configured to sense the value of the blood pressure within at least one of a chamber of a heart or an artery of the patient, wherein the arrhythmia discrimination module is configured to receive the value of the blood pressure from the sensor.

22. The system of claim 21, wherein the sensor is configured to sense the value of the blood pressure within a right ventricle of the patient.

23. The system of claim 13, further comprising an implantable medical device, wherein the implantable medical device comprises the stimulation generator, the processor, and the arrhythmia discrimination module.

24. The system of claim 13, further comprising at least one lead including one or more electrodes, wherein the stimulation generator is configured to deliver the vagal stimulation to the patient via the one or more electrodes of the at least one lead.

25. A non-transitory computer-readable medium comprising instructions for causing a programmable processor to:

detect a tachycardia based on at least one value of a cardiac interval;
deliver vagal stimulation in response to the detection of the tachycardia;
sense a physiological parameter other than the cardiac interval during or subsequent to delivering vagal stimulation; and
classify the tachycardia as supraventricular or ventricular based on the sensed physiological parameter.

26. A system comprising:
means for detecting a tachycardia based on at least one value of a cardiac interval;
means for delivering vagal stimulation in response to the detection of the tachycardia;
means for sensing a physiological parameter other than the cardiac interval during or subsequent to delivering vagal stimulation; and
means for classifying the tachycardia as supraventricular or ventricular based on the sensed physiological parameter.

27. A method comprising:
detecting a tachycardia based on at least one value of a cardiac interval;
delivering vagal stimulation in response to the detection of thetachycardia;
sensing a physiological parameter during or subsequent to delivering vagal stimulation;
classifying the tachycardia as supraventricular based on the sensed physiological parameter; and
providing an indication to the user based on the classification of supraventricular tachycardia.

28. The system of claim 13, wherein the arrhythmia discrimination module is configured to:
determine a value of the physiological parameter after detecting the tachycardia and prior to the vagal stimulation;
determine if the detected physiological parameter during or subsequent to the vagal stimulation has changed relative to a value prior to the vagal stimulation; and
classify the tachycardia as supraventricular in response to determining the detected physiological parameter has changed relative to the value prior to the vagal stimulation.

29. The system of claim 28, wherein the arrhythmia detection module is configured to control the stimulation generator to deliver the vagal stimulation during an atrial refractory period.

30. A system comprising:
a stimulation generator configured to deliver vagal stimulation to a patient;
a processor configured to detect a tachycardia based on at least one value of a cardiac interval;
an arrhythmia discrimination module configured to control the stimulation generator to deliver the vagal stimulation in response to the detection of the tachycardia, detect a physiological parameter other than the cardiac interval during or subsequent to the stimulation generator delivering the vagal stimulation, and classify the tachycardia as supraventricular or ventricular based on the detected physiological parameter; and
a sensor configured to sense a value of a blood pressure of the patient,
wherein the physiological parameter comprises the value of a blood pressure of the patient,
the arrhythmia discrimination module further configured to classify the tachycardia based on the value of the blood pressure detected during or subsequent to the vagal stimulation if the value of the cardiac interval is not increased during or subsequent to the vagal stimulation.

31. The system of claim 30, wherein the arrhythmia discrimination module is further configured to classify the tachycardia as supraventricular based on a decrease in the value of the blood pressure and the value of the cardiac interval is not increased during or subsequent to the vagal stimulation.

32. The system of claim 31, wherein the sensor is an implantable sensor and the blood pressure is a ventricular pressure.

* * * * *